US00PP32535P2

(12) United States Plant Patent
Weber

(10) Patent No.: US PP32,535 P2
(45) Date of Patent: Dec. 1, 2020

(54) STRAWBERRY PLANT NAMED 'DICKENS'

(50) Latin Name: ***Fragaria* x &ananassa**
Varietal Denomination: Dickens

(71) Applicant: CORNELL UNIVERSITY, Ithaca, NY (US)

(72) Inventor: Courtney A. Weber, Geneva, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/602,080

(22) Filed: Aug. 1, 2019

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 5/08; A01H 6/7409
See application file for complete search history.

*Primary Examiner* — Keith O. Robinson
(74) *Attorney, Agent, or Firm* — Troutman Pepper Hamilton Sanders LLP (Rochester)

(57) ABSTRACT

This invention relates to a new and distinct June-bearing (short day responsive) strawberry plant named 'Dickens' primarily adapted to the growing conditions of the west central New York and other regions of similar climate. The new plant is primarily characterized by strong vigor, high resistance to replant diseases, fruit equally broad and long, wide rounded conical fruit shape, large primary fruit with a small internal cavity, uniformly large secondary and tertiary fruit, high fruit numbers per fruiting lateral and plant, flat calyx and intense red fruit color externally and internally.

8 Drawing Sheets

Figure 1A:
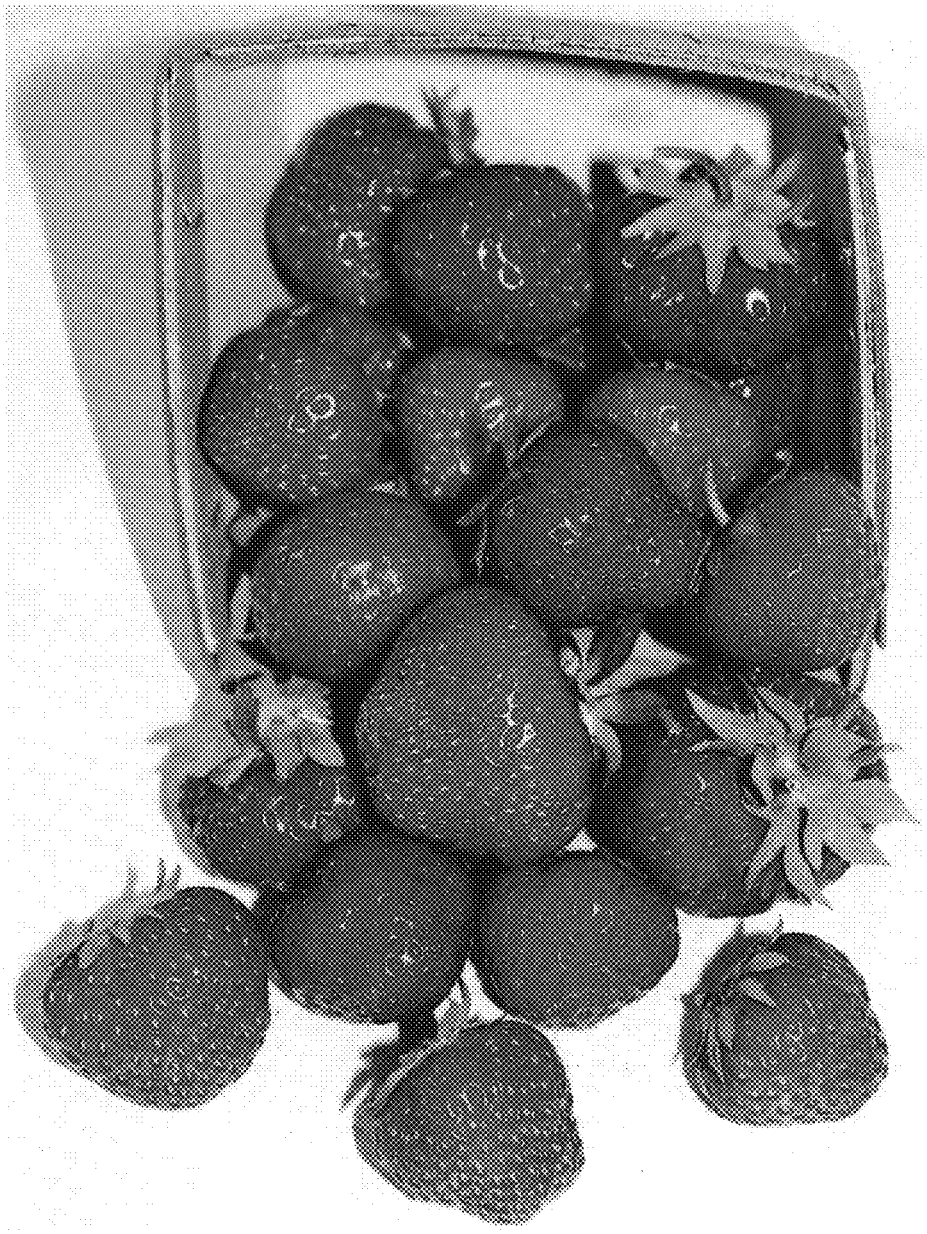

This invention was made with government support under grant number NYG-632421 awarded by the USDA. The government has certain rights in the invention.

FIELD

The present invention relates to a new and distinct June-bearing (short day responsive) strawberry plant designated as 'DICKENS'. The plant is botanically known as *Fragaria* x *ananassa* Duch. The new and distinct plant of strawberry originated from a hand-pollinated hybridization made in 2000 in Geneva, N.Y. between the female (seed bearing parent) 'Jewel' (U.S. Plant Pat. No. 5,897) and the male (pollen donor) parent 'Clancy' (U.S. Plant Pat. No. 16,571).

BACKGROUND

The new and distinct plant of strawberry originated from a hand-pollinated hybridization made in 2000 in Geneva, N.Y. between 'Jewel' (U.S. Plant Pat. No. 5,897) and 'Clancy' (U.S. Plant Pat. No. 16,571).

'Jewel' is June-bearing with average fruit size similar to 'Dickens' that is lighter red, firm fleshed, and with prominent wedge shaped primary berries that ripen in a similar season to 'Dickens'. 'Clancy' is June-bearing with larger average fruit size that is a similar red color, broad-conic shaped, firm fleshed and ripens in a similar season to 'Dickens'. Both parents of 'Dickens' are of the species *Fragaria* x *ananassa*. Thus, 'Dickens' is of the species *Fragaria* x *ananassa.*

The seeds resulting from this controlled hybridization were germinated in a greenhouse during the winter of 2000-01. The resulting seedlings were planted in the spring of 2001 in a field in Geneva, N.Y. and produced fruit in the summer of 2002. One, designated NY02-56, was selected for its large fruit size with an intense red color, firm flesh and high fruit number per plant. This new plant was discovered by the inventor, Courtney A. Weber.

During 2002, the original plant selection was propagated asexually by stolons (runners) at Geneva, N.Y. and a test planting of ten plants was established. Subsequently, larger test plantings have been established with asexually multiplied plants at Geneva, N.Y. The new plant was then tested over several years in the fruiting fields at Geneva, N.Y. Further propagation was done using tissue culture to produce disease free material for use in further testing. Tissue culture plants were used as mother plants for propagation from stolons. This propagation has demonstrated that the combination of traits disclosed herein as characterizing the new plant are fixed and remain true to type through successive generations of asexual reproduction. All propagules of 'Dickens' have been observed to be true to type in that during all asexual multiplication, the vegetative and fruit characteristics of the original plant have been maintained. All plants planted from dormant crowns or rooted runner tips have fruited after one season of growth in the field.

Test plantings in various locations in New York, Illinois, Minnesota, and Michigan have shown this plant to be widely adapted to differing soil and climactic conditions. It has shown cold hardiness typical to strawberries in a matted row system when covered with straw in the winter, which is standard procedure for this growing region. The first fruit of the new plant ripens at a similar period as both its parent 'Jewel' (U.S. Plant Pat. No. 5,897) and 'Clancy' (U.S. Plant Pat. No. 16,571) but produces peak harvest later than both parents with a longer overall harvest season.

SUMMARY

The new plant is primarily adapted to the climate and growing conditions of New York, the mid-western U.S, the Mid-Atlantic States, and southeastern Canada. This region provides the necessary summer conditions required for it to produce a strong vigorous plant and winter conditions required for chilling for production of fruit in the summer harvest season from May through July in open field conditions, depending on location.

The following list of traits in combination define the new plant as a unique plant distinguishing it from other commercial varieties in the region:

1. Tall plants with an upright growth habit and strong vigor;
2. predominantly trifoliate leaves with 4 and 5 leaflet leaves uncommonly present with high leaf gloss and broadly elliptical to obovate leaflets with greater length than width;
3. large primary fruit that is broader at the shoulder than long, with a rounded to wedge primary fruit shape, becoming more uniformly conic shaped in secondary and tertiary fruit as well as more evenly long and broad;
4. intense red fruit color, red flesh color with a ring of lighter red flesh surrounding a small cavity in primary fruit and rarely in secondary fruit, high fruit aroma, and high flesh firmness;
5. a generally flat calyx smaller in diameter than the fruit width;
6. medium sized stipule, generally light yellow-green in color and often blushed on young leaf petioles;
7. middle to late season production with high fruit numbers per plant and high yields; and
8. an extended harvest season compared to other short day responsive types grown in the region.

The varieties which are believed to most closely resemble 'Dickens' are 'Clancy' (U.S. Plant Pat. No. 16,571), 'L'Amour' (U.S. Plant Pat. No. 16,480), 'Ovation' (unpatented), and 'Jewel' (U.S. Plant Pat. No. 5,897).

In comparison to the similar plant 'Clancy', 'Dickens' differs by the following characteristics. The plant of 'Dickens' is taller with a wider growth habit and greater vigor. The fruit of 'Dickens' is smaller on average than that of 'Clancy' with two times more fruit per plant on average. The yield of 'Dickens' is larger than that of 'Clancy'. The fruit of 'Dickens' has higher soluble solids (% Brix) and higher titratable acids than that of 'Clancy' with lower juice pH. The harvest season of 'Dickens' begins similarly to that of 'Clancy' but peaks later and is more extended in duration.

In comparison to the similar plant, 'L'Amour', 'Dickens' differs by the following combination of characteristics. The terminal leaflets are wider and longer in length giving them a greater length to width ratio and a broadly elliptical to obovate shape and the plant canopy is less dense. The stipules of 'Dickens' are shorter and less wide than those of 'L'Amour' and more commonly pigmented, especially on young petioles. The fruiting trusses of 'Dickens' are shorter and the calyx is smaller than those of 'L'Amour'. The harvest season for 'Dickens' starts later than 'L'Amour' and is more extended in length.

In comparison to the similar plant, 'Ovation', 'Dickens' differs by the following combination of characteristics. The plant of 'Dickens' is shorter but broader than 'Ovation'. The fruit of 'Dickens' is smaller on average than 'Ovation' with a broader cross section resulting in a lower length to width ratio. The fruit of 'Dickens' has higher average soluble solids than 'Ovation' and a darker red fruit skin color. 'Dickens' is more resistant to late season powdery mildew compared to 'Ovation'. 'Dickens' produces a higher yield compared to 'Ovation' with an earlier peak harvest date but longer total harvest season length.

In comparison to the similar plant, 'Jewel', 'Dickens' differs by the following combination of characteristics. The plant of 'Dickens' is more vigorous and is broader and taller than 'Jewel'. The foliage is wider and longer in 'Dickens' compared to 'Jewel'. The stipules of 'Dickens' are shorter and less broad than those of 'Jewel'. 'Dickens' plants produce more fruit per plant on average than 'Jewel' and higher overall yield. The fruit of 'Dickens' is darker red in color than 'Jewel' with firmer flesh. The fruit of 'Dickens' has higher soluble solids, higher titratable acidity and lower juice pH than that of 'Jewel'. The fruit of 'Dickens' is smaller on average than that of 'Jewel'. The fruiting trusses of 'Dickens' are longer in overall length than those of 'Jewel'.

BRIEF DESCRIPTIONS OF THE DRAWINGS

The accompanying color photographs show typical specimens of the new plant at various stages of development as nearly true as it is possible to make in color reproductions. The depicted plant and plant parts were from the first harvest season, approximately 13 months after planting.

Figure 1B:
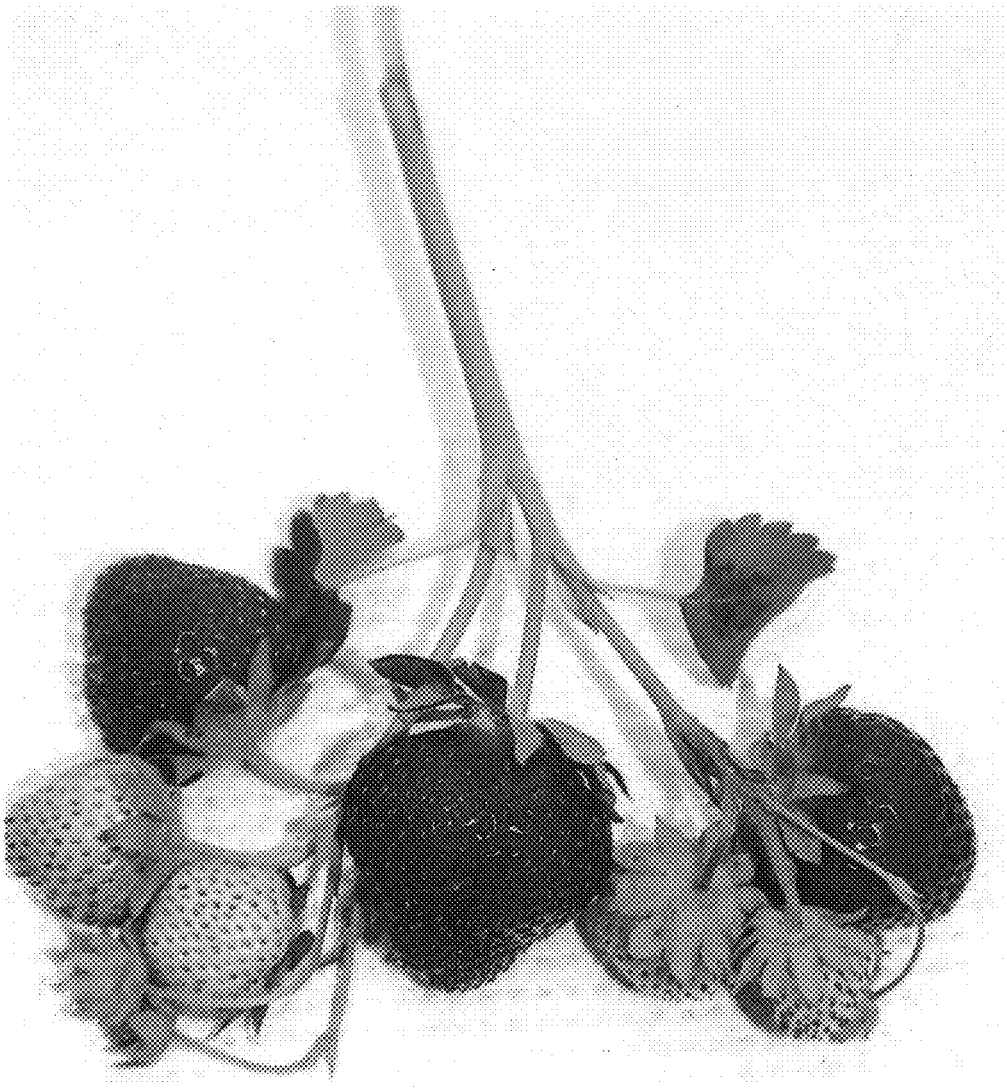

FIGS. 1A-B show typical fruit shape and uniformity (FIG. 1A) and fruiting truss arrangement including large peduncle bracts (FIG. 1B) of 'Dickens'.

Figure 2A:
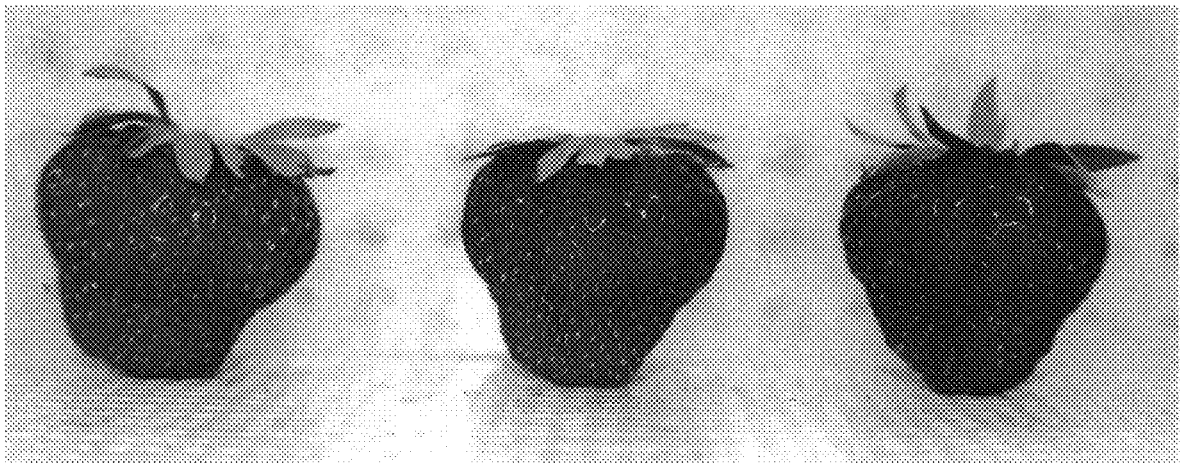
Figure 2B:
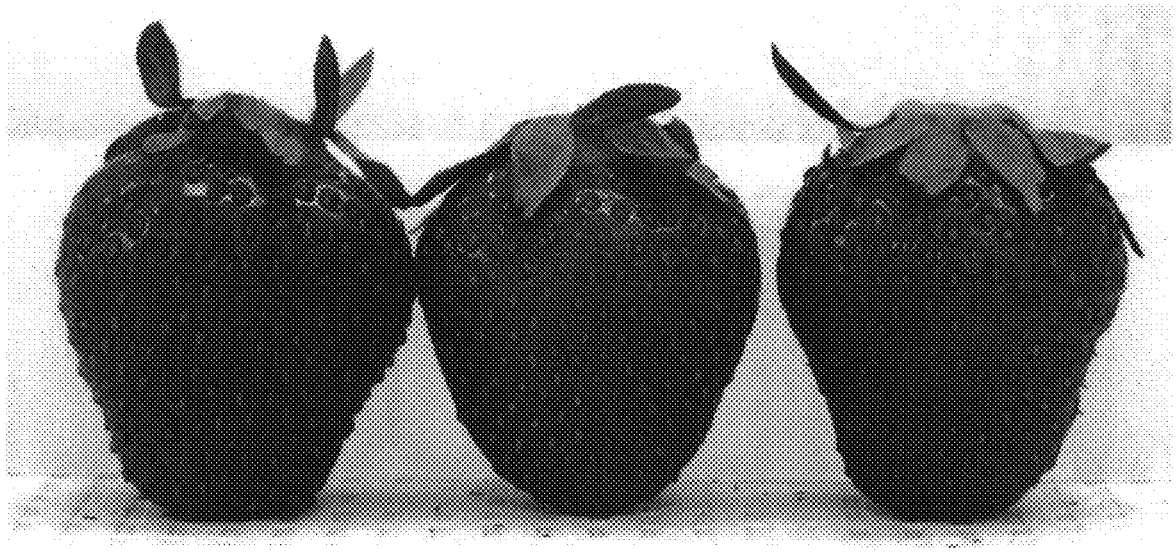
Figure 2C:
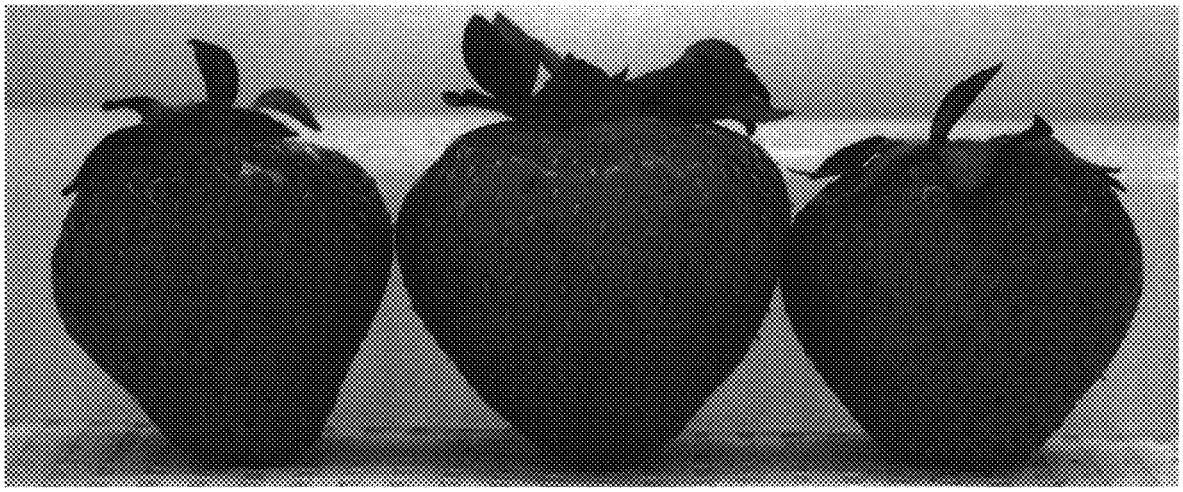

FIGS. 2A-C show typical external fruit characteristics of 'Dickens' (FIG. 2A) including calyx structure and fruit shape compared to 'Jewel' (FIG. 2B) and 'Clancy' (FIG. 2C).

Figure 3A:
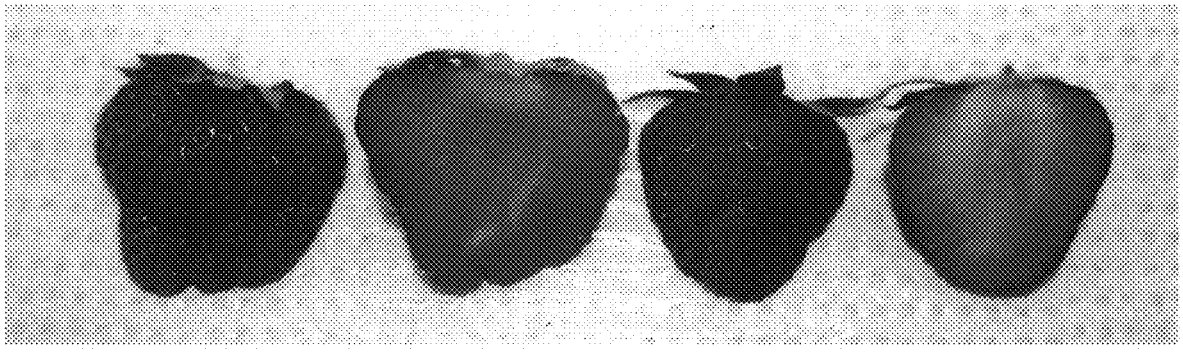
Figure 3B:
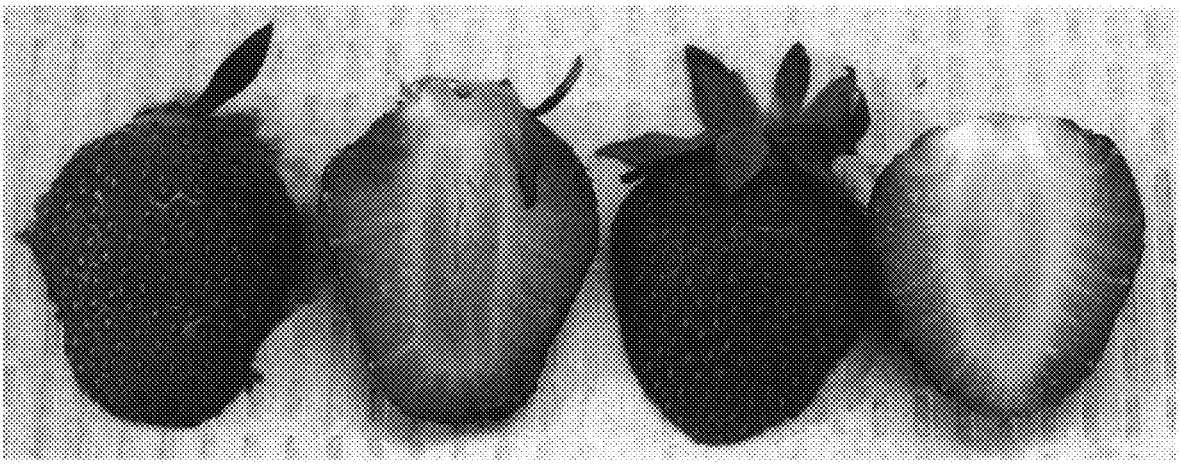
Figure 3C:
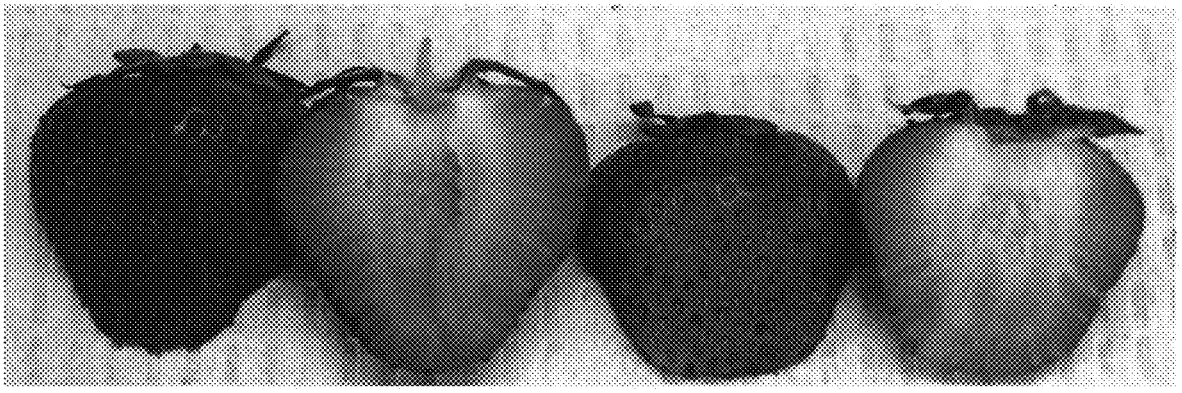

FIGS. 3A-C show typical internal fruit characteristics of 'Dickens' (FIG. 3A) compared to 'Jewel' (FIG. 3B) and 'Clancy' (FIG. 3C).

Figure 4A:
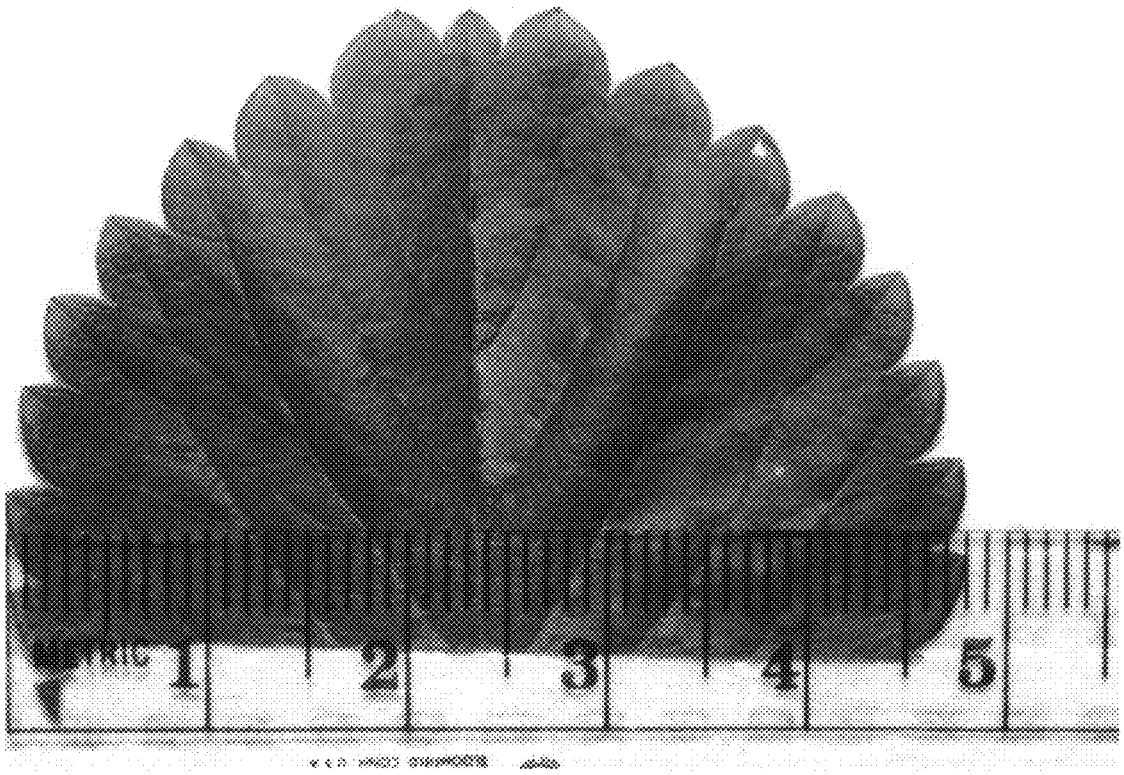
Figure 4B:
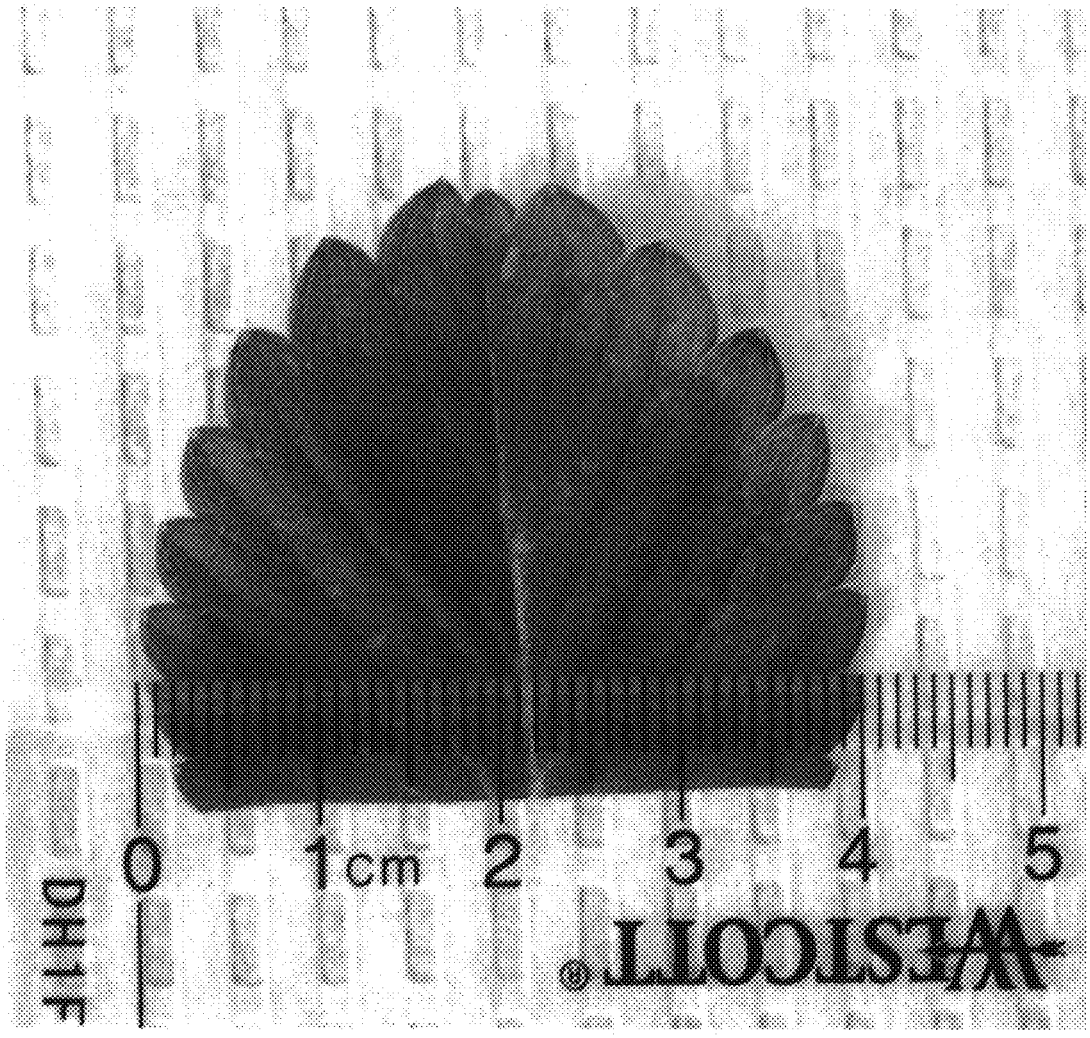
Figure 4C:
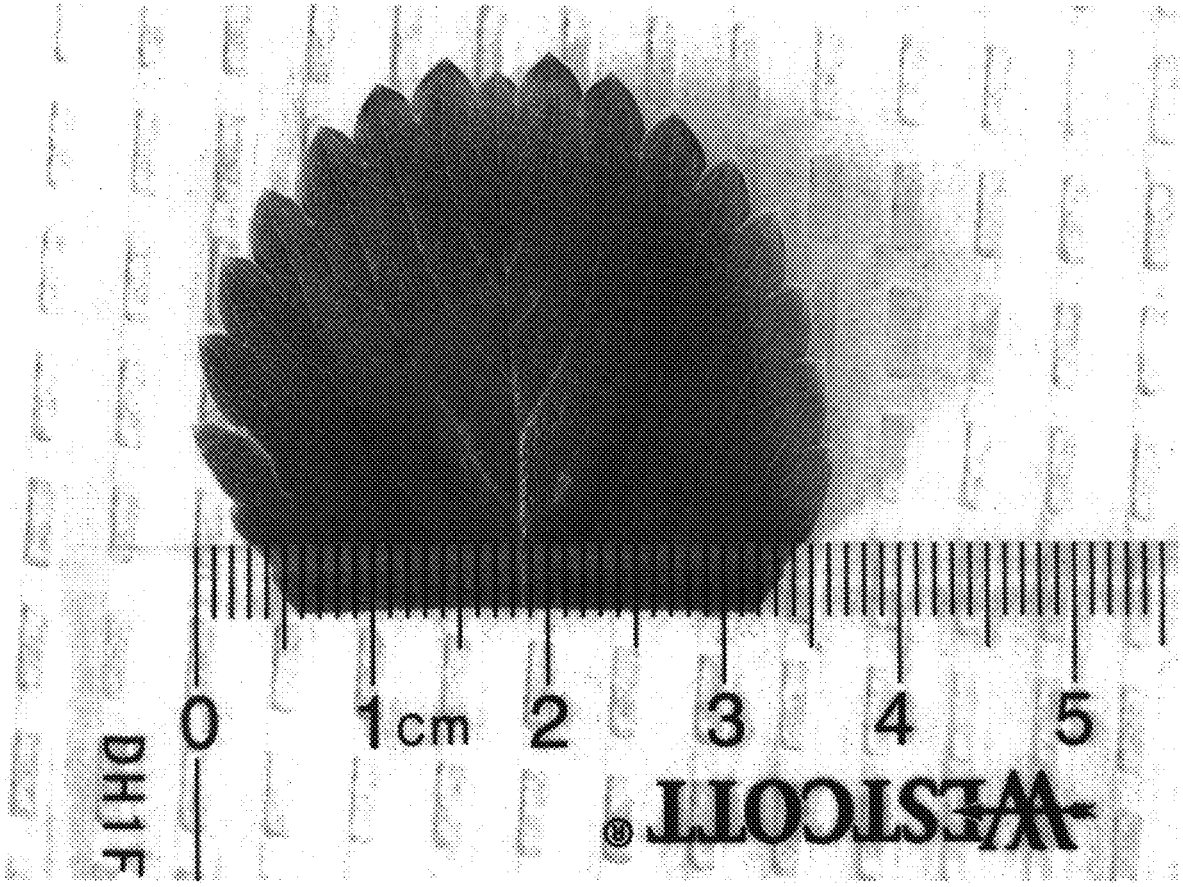

FIGS. 4A-C show leaf margin serrations for 'Dickens' (FIG. 4A), 'Jewel' (FIG. 4B) and 'L'Amour' (FIG. 4C).

DETAILED BOTANICAL DESCRIPTION

The following description of 'Dickens', unless otherwise noted, is based on observations taken during the 2018 growing season in Geneva, N.Y. These measurements and ratings were taken from plants planted in May 2017. The age of the planting was approximately 13 months and in its first harvest season. Yield observations and fruit quality characteristics are averaged from data collected during the 2013 and 2014 production seasons. The characteristics of the new plant may vary in detail, depending upon variations in environmental factors (temperature, rainfall, humidity and light intensity). 'Dickens' has not been observed under all possible environmental conditions. Color terminology where noted follows The Royal Horticultural Society Colour Chart ("R.H.S.C.C."), London, copyright 2001.

Comparative fruit characteristics: 'Dickens' fruit, fruit production, and fruit quality characteristics collected in the first harvest season after planting are shown in Tables 1-4.

TABLE 1

| Fruit characteristics: Yield (g/plant) | | | |
|---|---|---|---|
| Cultivar | 2013 | 2014 | Average |
| 'Dickens' | 446 | 235 | 341 |
| 'Clancy' | 192 | 225 | 209 |
| 'Ovation' | 209 | 270 | 240 |

TABLE 1-continued

| Fruit characteristics: Yield (g/plant) | | | |
|---|---|---|---|
| Cultivar | 2013 | 2014 | Average |
| 'Jewel' | 200 | 270 | 235 |
| 'Seneca' | 363 | 238 | 301 |

Total fruit yield of 'Dickens' and regionally standard varieties from 2 separate trials, one harvested in 2013 and one in 2014 in Geneva, NY. Fruit was harvested in June/July in each year. The plants of 'Dickens' and the other varieties were grown in a cooperating commercial nursery in Hartford, MI or South Deerfield, MA and planted the year prior for each trial in May 2012 and 2013 respectively.

TABLE 2

| Fruit characteristics: Weight (g per berry) and Number per plant | | | | |
|---|---|---|---|---|
| Cultivar | 2013 | 2014 | Average | Mean Fruit Number/Plant |
| 'Dickens' | 11.8 | 8.7 | 10.3 | 33 |
| 'Clancy' | 14.7 | 12.8 | 13.8 | 16 |
| 'Ovation' | 11.8 | 11.3 | 11.6 | 22 |
| 'Jewel' | 13.9 | 10.9 | 12.4 | 19 |
| 'Seneca' | 12.9 | 12.5 | 12.7 | 24 |

Average fruit weight and mean number of fruit per plant of 'Dickens' and regionally standard varieties from 2 separate trials, one harvested in 2013 and one in 2014 in Geneva, NY. Fruit was harvested in June/July in each year. The plants of 'Dickens' and the other varieties were grown in a cooperating commercial nursery in Hartford, MI or South Deerfield, MA and planted the year prior for each trial in May 2012 and 2013, respectively.

TABLE 3

| Fruit characteristics: Color and dimensions | | | | |
|---|---|---|---|---|
| Character | 'Dickens' | 'L'Amour' | 'Jewel' | 'Clancy' |
| RHSCC Exterior Color | red 46A | red 46B | red 44A | red 46A |
| Fruit Length mean (cm) | 3.23 | 4.22 | 3.46 | 3.07 |
| Fruit Width mean (cm)[1] | 3.27 | 3.62 | 3.61 | 3.59 |
| Fruit Length/ Width Ratio | 0.99 | 1.20 | 1.05 | 0.86 |
| No. Sepals/ Berry | 10.7 | 11.0 | 12.4 | 11.9 |

Comparison of mature secondary fruit characteristics of 'Dickens' with standards grown in Geneva, NY.
[1]Width is measured across the widest part of the berry, typically across the upper section.

TABLE 4

| Fruit characteristics: Chemical qualities | | | | |
|---|---|---|---|---|
| Character | 'Dickens' | 'L'Amour' | 'Jewel' | 'Clancy' |
| Soluble solids[1,2] | 10.54 | 8.91 | 7.80 | 9.02 |
| Titratable acidity[2,3] | 9.00 | 8.93 | 6.61 | 8.93 |
| Juice pH[2] | 3.35 | 3.68 | 3.44 | 3.54 |

Comparison of soluble solids (% Brix), titratable acidity, and juice pH of 'Dickens' with standards grown in Geneva, NY.
[1]Soluble solids is estimated from % Brix with % Brix being an indirect measurement of the sugar content in the fruit.
[2]Averaged from 3 samples on 3 dates during the harvest season.
[3]g per L equivalents of citric acid Detailed fruit characteristics of 'Dickens':

*Ratio of length/width*.—Broader than long to equal.

*Size*.—Large. Mean fruit size is 10.3 g.; maximum fruit size is 45.0 g.

*Aroma*.—Strong strawberry aroma.

*Predominant shape*.—Broad, conical.

*Difference in shapes between primary and secondary fruit*.—Low to moderate.

*Band without achenes*.—Narrow width.

*Color of mature fruit*.—Bright to dark red group 46A at maturity to red group 53A at over mature.

*Evenness of color*.—Usually even.

*Glossiness*.—Moderate to high.

*Insertion of achenes*.—Level to slightly recessed from surface.

*Attitude of the calyx segments*.—Usually flat with occasional reflexed.

*Size of calyx in relation to fruit diameter*.—Generally smaller.

*Adherence of calyx* (*when fully ripe*).—Strong.

*Firmness of skin*.—Strong.

*Firmness of flesh*.—Firm.

*Color of flesh*.—Intense red with slightly lighter inner ring (red group 46A to 44C).

*Distribution of red color of the flesh*.—Uniform through central with slightly lighter center.

*Hollow center*.—Weakly expressed in primary fruit. Generally not in secondary fruit.

*Seed color*.—Medium yellow-green to red on sun exposed side (yellow-green 154A to red 59A).

*Time of flowering* (50% *of plants at first flower*).—Mean first bloom date in Geneva, N.Y. is May 8; mean full bloom is May 14; mean last bloom is May 28.

*Time of ripening* (50% *of plants with first ripe fruit*).—Mean fruit harvest date in Geneva, N.Y. is June 11; mean last harvest is July 6; mean peak harvest is June 20.

*Type of bearing*.—Fully short day responsive.

Comparative plant characteristics: 'Dickens' plant characteristics are shown in Table 5. Plant characteristics are taken from a fully mature mid-season plant.

TABLE 5

| Plant characteristics: Comparisons | | | | |
|---|---|---|---|---|
| Character | 'Dickens' | 'L'Amour' | 'Jewel' | 'Clancy' |
| Plant Height (mean cm) | 31.6 | 31.9 | 27.3 | 26.1 |
| Vigor[1] | 7.0 | 8.3 | 5.0 | 7.0 |
| Canopy density[1] | 6.0 | 7.7 | 7.0 | 7.5 |

Comparison of plant characteristics of 'Dickens', with standards grown in Geneva, NY.
[1]Rated on a scale of 1-9 (9 being more vigorous or dense) in mature replicated plots.

Detailed plant characteristics of 'Dickens':

*Size*.—Large. Mean diameter of plants is 49 cm with a range of 45 to 54 cm. Mean height is 31.6 cm.

*Habit*.—Moderately upright.

*Density*.—Moderate.

*Vigor*.—Strong.

Comparative foliage characteristics: 'Dickens' foliage characteristics are shown in Table 6. Foliage characteristics are taken from a fully mature tri-foliate during mid-season.

TABLE 6

| Foliage characteristics: Comparisons | | | |
|---|---|---|---|
| Character | 'Dickens' | 'L'Amour' | 'Jewel' |
| RHSCC Color (upper surface) | green 137A | green 137A | green 138A |
| RHSCC Color (lower surface) | yellow-green 146B | green 139C | green 137D |

TABLE 6-continued

| Foliage characteristics: Comparisons | | | |
|---|---|---|---|
| Character | 'Dickens' | 'L'Amour' | 'Jewel' |
| Terminal Leaflet Length mean (cm) | 9.5 | 8.4 | 7.5 |
| Terminal Leaflet Width mean (cm) | 8.9 | 8.5 | 7.6 |
| Terminal Leaflet ratio (L/W) | 1.07 | 0.99 | 0.99 |
| Petiole Length mean (cm) | 23.2 | 22.8 | 19.9 |
| Serrations/Leaf | 22.9 | 22.3 | 18.3 |
| Stipule Length mean (cm) | 2.7 | 3.5 | 3.0 |
| Stipule Width mean (cm) | 0.6 | 0.8 | 0.8 |

Comparison of leaf characteristics of 'Dickens' to standards grown in Geneva, NY.

Detailed foliage characteristics of 'Dickens':

*Color of upper surface*.—Green group 137A.

*Color of underside*.—Yellow-green group 146B.

*Shape in cross section*.—Slightly concave.

*Interveinal blistering*.—Light to moderate

*Glossiness*.—Low.

*Number of leaflets/leaf*.—Generally three.

*Leaf blistering*.—Weak to medium leaf blistering.

Terminal leaflet:

*Size*.—Large. Mean length is 9.5 cm; mean width is 8.9 cm.

*Length/width ratio*.—Longer than broad; 9.5 cm/8.7 cm=1.07.

*Shape of base*.—Cuneate.

*Shape serrations*.—Mucronate.

Petiole:

*Pubescence density*.—High.

*Stipule color*.—Light to medium yellow-green (yellow-green N145B).

*Anthocyanin coloration of stipule*.—Common on young leaves. (red 46B).

*Attitude of hairs*.—Generally toward petiole base.

*Size of bract leaflets*.—Mediums size. Mean length: 28.6 mm/2.9 cm, ranging from 22 mm to 35 mm; mean width: 18.8 mm/1.9 cm, ranging from 7 mm to 30 mm.

*Frequency of bract leaflets*.—Occur on approximately 20% of petioles.

Comparative flower and inflorescence characteristics: 'Dickens' inflorescence and flower characteristics. Inflorescence characteristics are taken from a fully mature plant during full bloom. Flower characteristics are taken from a secondary flower during mid-season at full maturity:

TABLE 7

| Flower and Inflorescence Characteristics: Comparisons | | | |
|---|---|---|---|
| Character | 'Dickens' | 'L'Amour' | 'Jewel' |
| Fruiting Truss Length (mean cm)[1] | 25.6 | 32.3 | 20.9 |
| Corolla Diameter (mean mm) | 24.3 | 36 | 31 |
| Calyx Diameter (mean mm) | 26.9 | 33 | 34 |
| Petal Length (mean mm) | 10.6 | 15.4 | 14.0 |
| Petal Width | 9.1 | 13.6 | 13.3 |
| Petal L/W Ratio | 1.17 | 1.13 | 1.09 |
| Petals/Flower (mean) | 5.0 | 5.1 | 6.3 |
| Sepals/Flower (mean) | 10.7 | 11.0 | 12.4 |

Comparison of inflorescence and secondary flower characteristics of 'Dickens' with standards grown in Geneva, NY.

[1]as measured from the base of the primary peduncle where it attaches to the crown of the plant to the furthest berry.

Detailed inflorescence characteristics of 'Dickens':

*Position relative to foliage*.—Generally below canopy.

*Fruiting truss length*.—Medium; mean length of 25.6 cm.

*Peduncle bract*.—Common. Often 2 or more on truss branches.

Detailed flower characteristics of 'Dickens':

*Color*.—White (white 155C).

*Size*.—Medium to large. Mean corolla size/diameter is 2.43 cm (24.3 mm) and mean calyx size/diameter is 2.69 cm (26.9 mm).

*Size of calyx relative to corolla*.—Generally larger.

*Relative position of petals*.—Overlapping in primary fruit. No overlap in secondary fruit.

*Petal length/width ratio*.—Longer than broad. Mean petal length to width ratio is 1.17.

*Petal shape*.—Obovate.

*Stamens*.—Stamens are present in the flower.

*Pest reactions*.—'Dickens' is known to be moderately resistant to the two-spotted spider mite (*Tetranychus urticae*) and susceptible to aphids (*Chaetosiphon fragaefolii*) and flower thrips (*Frankliniella occidentalis* and *F. tritici*). It is somewhat susceptible to leaf spot (*Mycosphaerella fragariae*) and tolerant to leaf blight (Phomopsis obscurans). It is resistant to leaf scorch (*Diplocarpon earliana*) and foliar powdery mildew (*Podosphaera aphanis*) in mid-summer. It is tolerant or resistant to common root rot complexes found in NY and is tolerant to replant disease. The susceptibility of the new plant to any of the virus complexes of NY has not been determined.

What is claimed:

1. A new and distinct cultivar of strawberry plant named 'Dickens' as herein described and illustrated by the characteristics set forth above.

* * * * *